(12) United States Patent
Arnholt et al.

(10) Patent No.: US 9,415,206 B2
(45) Date of Patent: Aug. 16, 2016

(54) METHOD FOR COATING DEVICES USING ELECTROSPINNING

(71) Applicant: Cardiac Pacemakers, Inc., St. Paul, MN (US)

(72) Inventors: Devon N. Arnholt, Shoreview, MN (US); Douglas D. Pagoria, Forest Lake, MN (US); Jeannette C. Polkinghorne, Spring Lake Park, MN (US); Joseph T. Delaney, Jr., Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/825,166

(22) Filed: Aug. 12, 2015

(65) Prior Publication Data

US 2015/0343200 A1 Dec. 3, 2015

Related U.S. Application Data

(63) Continuation of application No. 14/556,818, filed on Dec. 1, 2014, now Pat. No. 9,132,269, which is a continuation of application No. 13/571,553, filed on Aug. 10, 2012, now Pat. No. 8,903,506.

(60) Provisional application No. 61/523,069, filed on Aug. 12, 2011.

(51) Int. Cl.
*A61N 1/05* (2006.01)
*D01D 5/00* (2006.01)

(52) U.S. Cl.
CPC *A61N 1/05* (2013.01); *A61N 1/056* (2013.01); *D01D 5/0023* (2013.01); *D01D 5/0084* (2013.01); *D10B 2321/08* (2013.01);

(Continued)

(58) Field of Classification Search
CPC ......... A61N 1/05; A61N 1/04; A61N 1/0565; A61N 1/0568; A61N 1/0551; A61N 1/08; A61N 2001/086; A61B 2562/125; A61B 5/042

See application file for complete search history.

(56) References Cited

U.S. PATENT DOCUMENTS 7,689,291 B2 3/2010 Polkinghorne et al.
7,908,016 B2 3/2011 Atanasoska et al.
8,903,506 B2 12/2014 Arnholt et al.

(Continued)

FOREIGN PATENT DOCUMENTS

AU 2012295332 B2 12/2014
GB 1527592 A 10/1978

(Continued)

OTHER PUBLICATIONS

Hong, Lingfei; Pan, Tingrui, "Photopatternable Superhydrophobic Nanocomposites for Microfabrication," Journal of Microelectromechanical Systems, vol. 19, No. 2, (Apr. 2010), pp. 246-253.

(Continued)

*Primary Examiner* — Rex R Holmes
(74) *Attorney, Agent, or Firm* — Faegre Baker Daniels LLP (57) ABSTRACT

A medical electrical lead may include an insulative lead body, a conductor disposed within the insulative lead body, an electrode disposed on the insulative lead body and in electrical contact with the conductor and a fibrous matrix disposed at least partially over the electrode. The fibrous matrix may be formed from polyether polyurethane.

18 Claims, 5 Drawing Sheets

(52) U.S. Cl.
CPC ......... *D10B2331/06* (2013.01); *Y10T 29/4922* (2015.01); *Y10T 29/49224* (2015.01)

(56) References Cited

U.S. PATENT DOCUMENTS

| | | |
|---|---|---|
| 8,965,531 B2 | 2/2015 | Arnholt et al. |
| 2005/0149158 A1 | 7/2005 | Hunter et al. |
| 2006/0264577 A1 | 11/2006 | Faust et al. |
| 2007/0051531 A1 | 3/2007 | Borgaonkar et al. |
| 2007/0067882 A1 | 3/2007 | Atanasoska et al. |
| 2007/0239245 A1* | 10/2007 | Borgaonkar et al. ......... 607/121 |
| 2007/0255378 A1 | 11/2007 | Polkinghorne et al. |
| 2008/0071338 A1 | 3/2008 | Jiang et al. |
| 2009/0076530 A1 | 3/2009 | Fukutomi et al. |
| 2009/0099441 A1 | 4/2009 | Giszter et al. |
| 2009/0099634 A1 | 4/2009 | Atanasoska et al. |
| 2009/0105796 A1 | 4/2009 | Atanasoska et al. |
| 2009/0326077 A1 | 12/2009 | Desai et al. |
| 2010/0023104 A1 | 1/2010 | Desai et al. |
| 2010/0057197 A1 | 3/2010 | Weber et al. |
| 2010/0069578 A1 | 3/2010 | Faust et al. |
| 2010/0179298 A1 | 7/2010 | Faust et al. |
| 2010/0241204 A1* | 9/2010 | Scheuermann ............... 607/116 |
| 2010/0241208 A1 | 9/2010 | Pinchuk |
| 2011/0021899 A1 | 1/2011 | Arps et al. |
| 2011/0054580 A1 | 3/2011 | Desai et al. |
| 2011/0054581 A1 | 3/2011 | Desai et al. |
| 2011/0137389 A1 | 6/2011 | Polkinghorne et al. |
| 2013/0013040 A1 | 1/2013 | Desai et al. |
| 2013/0041442 A1 | 2/2013 | Arnholt et al. |
| 2013/0131765 A1 | 5/2013 | Polkinghorne et al. |
| 2013/0231733 A1 | 9/2013 | Knisley et al. |
| 2013/0238086 A1 | 9/2013 | Ballard et al. |
| 2013/0268062 A1 | 10/2013 | Puckett et al. |
| 2014/0324141 A1 | 10/2014 | Arnholt et al. |
| 2015/0025608 A1 | 1/2015 | Delaney et al. |
| 2015/0088238 A1 | 3/2015 | Arnholt et al. |

FOREIGN PATENT DOCUMENTS

| | | |
|---|---|---|
| JP | 2004119113 A | 4/2004 |
| JP | 2007154336 A | 6/2007 |
| JP | 2008515611 A | 5/2008 |
| JP | 2008253297 A | 10/2008 |
| JP | 2009000100 A | 1/2009 |
| JP | 2009507577 A | 2/2009 |
| JP | 2009531140 A | 9/2009 |
| JP | 2009535182 A | 10/2009 |
| JP | 2009540873 A | 11/2009 |
| JP | 2010540105 A | 12/2010 |
| SU | 132800 A | 1/1960 |
| WO | WO9008466 A1 | 8/1990 |
| WO | WO02089909 A1 | 11/2002 |
| WO | WO03045875 A1 | 6/2003 |
| WO | WO03101505 A1 | 12/2003 |
| WO | WO2004041529 A1 | 5/2004 |
| WO | WO2005032400 A2 | 4/2005 |
| WO | WO2005039664 A2 | 5/2005 |
| WO | WO2005065578 A2 | 7/2005 |
| WO | WO2005079339 A2 | 9/2005 |
| WO | WO2006020425 A1 | 2/2006 |
| WO | WO2006123340 A2 | 11/2006 |
| WO | WO2007003199 A1 | 1/2007 |
| WO | WO2007030722 A1 | 3/2007 |
| WO | WO2007109007 A1 | 9/2007 |
| WO | WO2007130900 A2 | 11/2007 |
| WO | WO2008008266 A2 | 1/2008 |
| WO | WO2008021020 A1 | 2/2008 |
| WO | WO2008036460 A1 | 3/2008 |
| WO | WO2008055038 A2 | 5/2008 |
| WO | WO2008060333 A1 | 5/2008 |
| WO | WO2008066538 A1 | 6/2008 |
| WO | WO2008066912 A2 | 6/2008 |
| WO | WO2008066914 A1 | 6/2008 |
| WO | WO2009002984 A2 | 12/2008 |
| WO | WO2009140381 A1 | 11/2009 |
| WO | 2010053585 A1 | 5/2010 |
| WO | 2010107967 A1 | 9/2010 |
| WO | WO2010065484 A1 | 10/2010 |
| WO | 2011017695 A1 | 2/2011 |
| WO | 2011017698 A1 | 2/2011 |
| WO | 2011028873 A2 | 3/2011 |
| WO | 2013112793 A1 | 8/2013 |
| WO | 2013151778 A1 | 10/2013 |

OTHER PUBLICATIONS

Huang, Zheng-Ming et al., "A review on polymer nanofibers by electrospinning and their applications in nanocomposites", Composites Science and Technology, No. 66, 2003, pp. 2223-2253.
International Preliminary Report on Patentability, Chapter II, issued in PCT/US2012/050260, completed Oct. 28, 2013, 16 pages.
International Preliminary Report on Patentability, Chapter II, issued in PCT/US2012/065896, mailed Dec. 18, 2013, 8 pages.
International Search Report and Written Opinion issued in PCT/US2012/050260, mailed Dec. 7, 2012, 12 pages.
International Search Report and Written Opinion issued in PCT/US2012/065896, mailed Feb. 20, 2013, 9 pages
Lee, J. L., "Polymer Nanoengineering for Biomedical Applications", Annals of Biomedical Engineering,34(1), (2006), 75-88.
Menini, Richard, et al., "Production of superhydrophobic polymer fibers with embedded particles using the electrospinning technique," Society of Chemical Industry, Polym Int 57, pp. 77-84 (2008), DOI: 10.1002/pi.
Su, Ching-Iuan et al., "A Study of Hydrophobic Electrospun Membrane Applied in Seawater Desalination by Membrane Distillation," Fibers and Polymers (2012), vol. 13, No. 6, pp. 698-702. DOI 10.1007/s12221-012-0698-3.
Written Opinion of the International Preliminary Examining Authority issued in PCT/US2012/050260, mailed Jul. 18, 2013, 7 pages.
Zhou, Tao; Yao, Yongyi; Xiang, Ruili; Wu, Yurong, "Formation and characterization of polytetrafluoroethylene nanofiber membranes for vacuum membrane distillation," Journal of Membrane Science 453 (2014), pp. 402-408. <www.elsevier.com/locate.memsci>.

\* cited by examiner

METHOD FOR COATING DEVICES USING ELECTROSPINNING

CROSS-REFERENCE TO RELATED APPLICATIONS

This application is a continuation of U.S. application Ser. No. 14/556,818, filed Dec. 1, 2014, issued on Sep. 15, 2015, as U.S. Pat. No. 9,132,269, which is a continuation of U.S. application Ser. No. 13/571,553, filed Aug. 10, 2012, which issued as U.S. Pat. No. 8,903,506 on Dec. 2, 2015, and which claims priority to U.S. Provisional Application 61/523,069, filed Aug. 12, 2011, each of which is commonly owned and is incorporated herein in its entirety by reference.

TECHNICAL FIELD

The present invention relates to methods for manufacturing medical devices. More specifically, the invention relates to methods for coating medical devices and to coated medical devices.

BACKGROUND

Cardiac pacing leads are well known and widely employed for carrying pulse stimulation signals to the heart from a battery operated pacemaker, or other pulse generating means, as well as for monitoring electrical activity of the heart from a location outside of the body. Electrical energy is applied to the heart via an electrode to return the heart to normal rhythm. Some factors that affect electrode performance include polarization at the electrode/tissue interface, electrode capacitance, sensing impedance, and voltage threshold. In all of these applications, it is highly desirable to optimize electrical performance characteristics at the electrode/tissue interface.

Recognized performance challenges of materials conventionally used as electrodes include difficulty controlling tissue in-growth, inflammation in the vicinity of the implanted device and/or the formation of fibrous scar tissue. These challenges may lead to difficulty in extracting the lead and/or reduced electrode performance over time.

SUMMARY

Disclosed herein are various embodiments of a coated medical device, as well as methods for coating medical devices.

In Example 1, a medical electrical lead includes an insulative lead body extending from a distal region to a proximal region. A conductor is disposed within the insulative lead body and extends from the proximal region to the distal region. An electrode is disposed on the insulative lead body and is in electrical contact with the conductor. A non-conductive fibrous matrix including polyether polyurethane is disposed at least partially over the electrode. The fibrous matrix has an average fiber diameter between 40 nanometers and 800 nanometers, and an average thickness of between about 2.54 microns and about 254 microns.

In Example 2, the medical electrical lead according to Example 1, wherein the fibrous matrix comprises electrospun polyether polyurethane.

In Example 3, the medical electrical lead according to any of Examples 1-2, wherein the fibrous matrix has sufficient fiber-to-fiber spacing to deliver electrophysiological therapy through the matrix.

In Example 4, the medical electrical lead according to any of Examples 1-3, wherein the fibrous matrix has an average fiber-to-fiber spacing between about 10 microns to about 50 microns.

In Example 5, the medical electrical lead according to any of Examples 1-4, wherein the fibrous matrix has an average fiber-to-fiber spacing between about 10 microns to about 25 microns.

In Example 6, the medical electrical lead according to any of Examples 1-5, further including a material on a surface of the fibrous matrix, wherein the material increases wettability of the surface as compared to the surface without the material.

In Example 7, the medical electrical lead according to any of Examples 1-6, wherein the coating material is poly(ethylene glycol)dimethacrylate.

In Example 8, method of forming a medical electrical lead having an insulative lead body and an electrode disposed on the insulative lead body includes forming a fibrous matrix comprising polyether polyurethane polymer by electrospinning; and disposing the fibrous matrix at least partially over the electrode. The fibrous matrix has an average fiber diameter between 40 nanometers and 800 nanometers and an average thickness between about 2.54 microns and 254 microns.

In Example 9, the method according to Example 8, wherein forming the fibrous matrix comprises forming the fibrous matrix directly onto the electrode.

In Example 10, the method according to any of Examples 8-9, wherein forming the fibrous matrix comprises forming the fibrous matrix on a substrate and then depositing the fibrous matrix at least partially over the electrode.

In Example 11, the method according to any of Examples 8-10, further including treating a surface of the fibrous matrix with a material that increases wettability of the surface as compared to the surface prior to treating.

In Example 12, the method according to Example 11, wherein the material is poly(ethylene glycol)dimethacrylate.

In Example 13, the method according to any of Examples 8-12, wherein the fibrous matrix has sufficient fiber-to-fiber spacing to deliver electrophysiological therapy through the matrix.

In Example 14, the method according to any of Examples 8-13, wherein the fibrous matrix has an average fiber-to-fiber spacing between about 10 microns to about 50 microns.

In Example 15, the method according to any of Examples 8-14, wherein the fibrous matrix has an average fiber-to-fiber spacing between about 10 microns to about 25 microns.

In Example 16, a medical electrical lead includes an insulative lead body, a conductor, an electrode, and a fibrous matrix. The insulative lead body extends from a distal region to a proximal region. The conductor is disposed within the insulative lead body and extends from the proximal region to the distal region. The electrode is disposed on the insulative lead body and in electrical contact with the conductor. The fibrous matrix includes electrospun polyether polyurethane disposed at least partially over the electrode. The fibrous matrix has an average fiber diameter between 40 nanometers and 800 nanometers.

In Example 17, the medical electrical lead according to Example 16, further including a material on a surface of the fibrous matrix, wherein the material increases wettability of the surface as compared to the surface without the material.

In Example 18, the medical electrical lead according to any of Examples 16-17, wherein the fibrous matrix has an average fiber-to-fiber spacing between about 10 microns to about 50 microns.

In Example 19, the medical electrical lead according to any of Examples 16-18, wherein the fibrous matrix further includes dopant material to facilitate polymer conductivity.

In Example 20, the medical electrical lead according to any of Examples 16-19, wherein the dopant material is less than 5 weight percent of the fibrous matrix While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
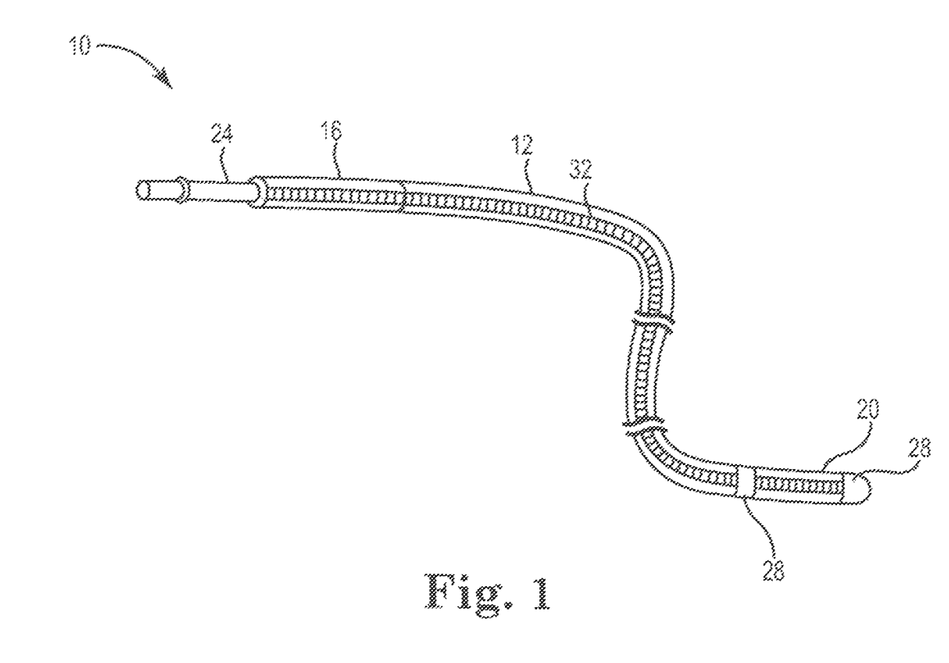
FIG. 1 is a schematic view of a medical electrical lead according to embodiments of the present invention.

FIG. 1 is a partial cross-sectional view of a medical electrical lead 10, according to various embodiments of the present disclosure. According to some embodiments, the medical electrical lead 10 can be configured for implantation within a patient's heart. According to other embodiments, the medical electrical lead 10 is configured for implantation within a patient's neurovascular regions. In yet another embodiment, the lead 10 can be a lead for a cochlear implant. The medical electrical lead 10 includes an elongated, insulative lead body 12 extending from a proximal end 16 to a distal end 20. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors are employed, the lead can include a combination of coiled and cable conductors. When a coiled conductor is employed, according to some embodiments, the conductor can have either a co-radial or a co-axial configuration.

The lead body 12 is flexible, but substantially non-compressible along its length, and has a circular cross-section. According to one embodiment of the present disclosure, an outer diameter of the lead body 12 ranges from about 2 to about 15 French. In many embodiments, the lead body 12 does not include a drug collar or plug.

The medical electrical lead 10 can be unipolar, bipolar, or multi-polar depending upon the type of therapy to be delivered. In embodiments of the present disclosure employing multiple electrodes 28 and multiple conductors 32, each conductor 32 is adapted to be connected to an individual electrode 28 in a one-to-one manner allowing each electrode 28 to be individually addressable. Additionally, the lead body 12 can include one or more lumens adapted to receive a guiding element such as a guidewire or a stylet for delivery of the lead 10 to a target location within a patient's heart.

The electrodes 28 can have any electrode configuration as is known in the art. According to one embodiment of the present disclosure, at least one electrode can be a ring or partial ring electrode. According to another embodiment, at least one electrode 28 is a shocking coil. According to yet another embodiment of the present disclosure, at least one electrode 28 includes an exposed electrode portion and an insulated electrode portion. In some embodiments, a combination of electrode configurations can be used. The electrodes 28 can be coated with or formed from platinum, stainless steel, titanium, tantalum, palladium, MP35N, other similar conductive material, alloys of any of the foregoing including platinum-iridium alloys, and other combinations of the foregoing including clad metal layers or multiple metal materials.

According to various embodiments, the lead body 12 can include one or more fixation members for securing and stabilizing the lead body 12 including the one or more electrodes 28 at a target site within a patient's body. The fixation member(s) can be active or passive. An exemplary active fixation member includes a screw-in fixation member. Examples of passive fixation members can include preformed distal portions of the lead body 12 adapted to bear against vessel walls and/or expandable tines provided at the distal end of the lead body 12.

Figure 2A:
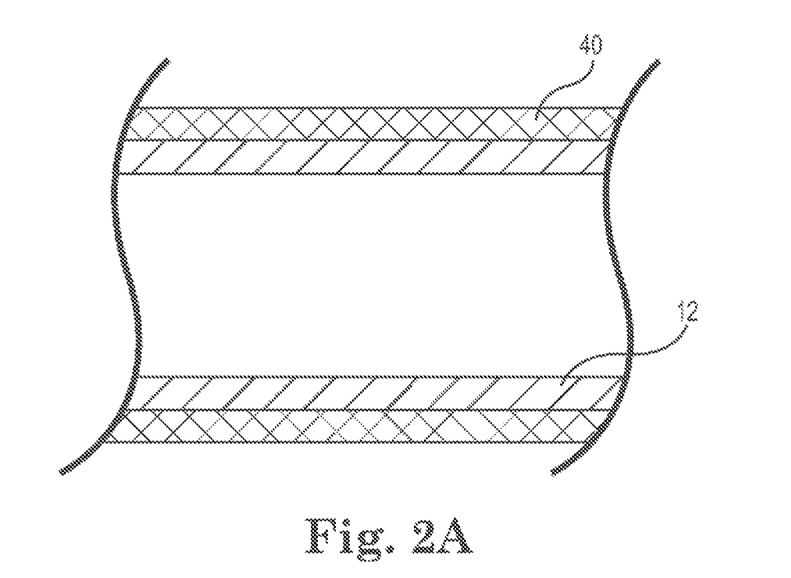
FIGS. 2A and 2B are schematic longitudinal cross-sections of a medical electrical lead according to embodiments of the present invention.
Figure 2B:
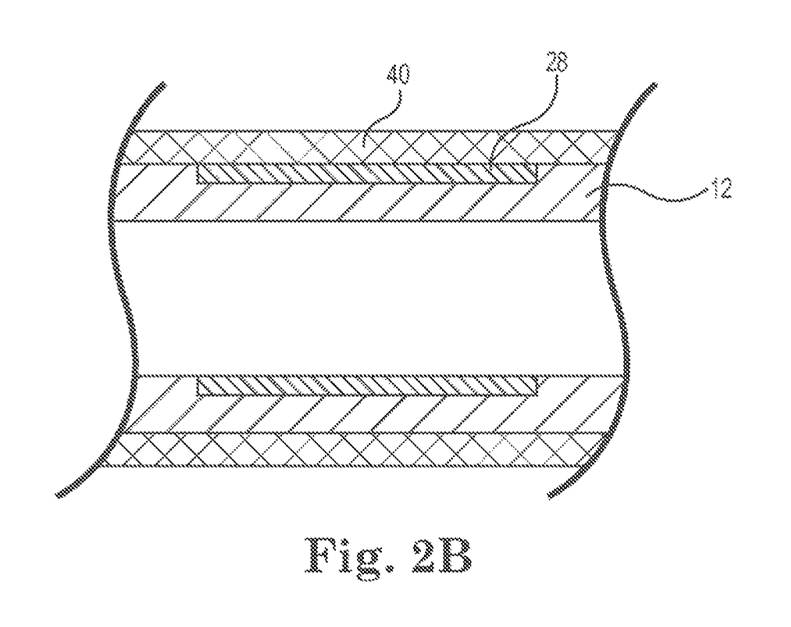

The lead 10 includes a fibrous matrix that is disposed over various parts of the insulative lead body 12. FIGS. 2A and 2B provide illustrative but non-limiting examples of regions of the lead 10 that may include a fibrous matrix. FIGS. 2A and 2B are schematic longitudinal cross-sectional views of the lead 10 of FIG. 1, in which internal structure has been removed for clarity.

FIG. 2A shows a fibrous matrix 40 disposed over a portion of the insulative lead body 12. The illustrated portion of the insulative lead body 12 may be adjacent an electrode such as the electrode 28, or it may be spaced apart from the electrodes. In contrast, FIG. 2B illustrates a fibrous matrix 40 disposed over the electrode 28. While the fibrous matrix 40 is illustrated as covering all of the electrode 28, in some embodiments the fibrous matrix 40 covers only a small portion of the electrode 28, a substantial portion of the electrode 28, or an intervening fraction of the electrode 28.

In some embodiments, the fibrous matrix 40 may provide various beneficial functionalities to the lead 10. In some embodiments, the fibrous matrix 40 may improve the abrasion resistance of the lead 10. In some embodiments, the fibrous matrix 40 may improve the electrical or thermal insulation of the lead 10. In some embodiments, the fibrous matrix 40 may provide improved control over tissue ingrowth, particularly at the site of the electrode 28. In certain embodiments, the amount of tissue ingrowth may be determined by tissue extraction in which the force required to remove an implanted lead 10 is measured with an Instron force gauge. In some embodiments, the thickness and average fiber diameter of fibrous matrix 40 impacts tissue ingrowth. The thickness and average fiber diameter of fibrous matrix 40 may also impact the ability to deliver electrophysiological therapy through fibrous matrix 40. In certain embodiments, the fibrous matrix 40 does not significantly impact the impedance of the lead 10.

The fibrous matrix 40 includes a plurality of randomly aligned fibers that comprise the matrix. In certain embodiments the fibrous matrix 40 may be formed by electrospinning or melt blowing, for example. The fibers may have diameters in the range of about 10-3000 nanometers (nm), for example. The fiber diameter size may be about 40-2000 nm, about 50-1500 nm or about 100-1000 nm, for example. The fiber diameter size may be measured by taking the average size of the fibers. In certain embodiments, the fibers may have diameters as little as 40 nm, 50 nm, 100 nm or 150 nm and as great as 300 nm, 400 nm, 500 nm, 600 nm, 650 nm, 700 nm, 725 nm, 750 nm or 800 nm or may be within any range delimited by any pair of the foregoing values. In other embodiments, the fibers may have an average diameter size less than about 800 nm, 750 nm, 725 nm, 700 nm, 600 nm, 500 nm or 400 nm. In other embodiments, the fiber matrix 40 may be formed partially or completely with hollow fibers using modified electrospinning and meltblowing techniques.

The fibrous matrix 40 may have an average fiber-to fiber-spacing in the range of about 1 to about 100 microns, more particularly from about 10 to about 50 microns, even more particularly from about 10 to about 25 microns. In some embodiments, the fiber spacing between adjacent fibers may be adjusted or regulated to control tissue ingrowth while minimizing impact on pacing capability. This can be accomplished, for example, by altering the deposition parameters or deposition material. In other embodiments, tissue in-growth is controlled by the thickness of the matrix. Suitable thicknesses for the fibrous matrix may range from about 0.00254 millimeters (mm) to about 0.254 mm (about 0.0001 inches (in.) to about 0.01 in.), more particularly from about 0.0127 mm to about 0.127 mm (about 0.0005 in. to about 0.005 in.), even more particularly from about 0.0254 mm to about 0.0762 mm (about 0.001 in. to about 0.003 in.).

In some embodiments, particularly when the fibrous matrix 40 is disposed at least partially over an electrode such as the electrode 28, the fibrous matrix 40 may have sufficient fiber spacing to permit ions to flow through the fibrous matrix 40 such that electrical contact may be made with the electrode 28.

A wide range of polymers may be used to prepare the fibrous matrix 40, including both conductive and non-conductive polymer materials. Suitable non-conductive polymers (i.e. polymers that are not intrinsically conductive) include homopolymers, copolymers and terpolymers of various polysiloxanes, polyurethanes, fluoropolymers, polyolefins, polyamides and polyesters. The non-conductive material in certain embodiments is free or substantially free of dopant materials that facilitate polymer conductivity. In other embodiments, the conductive material may comprises less than 5 weight percent (wt %) dopant, more particularly, less than 1 wt % dopant, even more particularly less than 0.5 wt % dopant. Suitable conductive polymers are disclosed in U.S. Pat. No. 7,908,016, which is incorporated herein by reference in its entirety.

In certain embodiments, the fibrous matrix 40 is formed from a non-conductive polyurethane material. Suitable polyurethanes may include polycarbonate, polyether, polyester and polyisobutylene (PIB) polyurethanes. Example suitable PIB polyurethanes are disclosed in U.S. published application 2010/0023104, which is incorporated herein by reference in its entirety. Further examples of such copolymers and methods for their synthesis are generally described in WO 2008/060333, WO 2008/066914, U.S. application Ser. No. 12/492,483 filed on Jun. 26, 2009, entitled POLYISOBUTYLENE URETHANE, UREA AND URETHANE/UREA COPOLYMERS AND MEDICAL DEVICES CONTAINING THE SAME, and U.S. application Ser. No. 12/874,887, filed Sep. 2, 2010, and entitled Medical Devices Including Polyisobutylene Based Polymers and Derivatives Thereof, all of which are incorporated herein by reference in their entirety. In other embodiments, the fibrous matrix 40 is formed from a non-conductive fluoropolymer material. Suitable fluoropolymer materials include polyvinylidene fluoride, poly(vinylidene fluoride-co-hexafluoropropene) (PVDF HFP), polytetrafluoroethylene and expanded polytetrafluoroethylene.

As described herein, the average diameter size of the fibrous matrix 40 may reduce tissue ingrowth. In some embodiments, the fibrous matrix 40 may include a polyurethane, such as a polycarbonate polyurethane and have an average diameter size of less than about 800 nm or less than about 750 nm. In other embodiments, the fibrous matrix 40 may include PVDF HFP and have an average diameter size of less than about 800 nm or less than about 730 nm.

Figure 3:
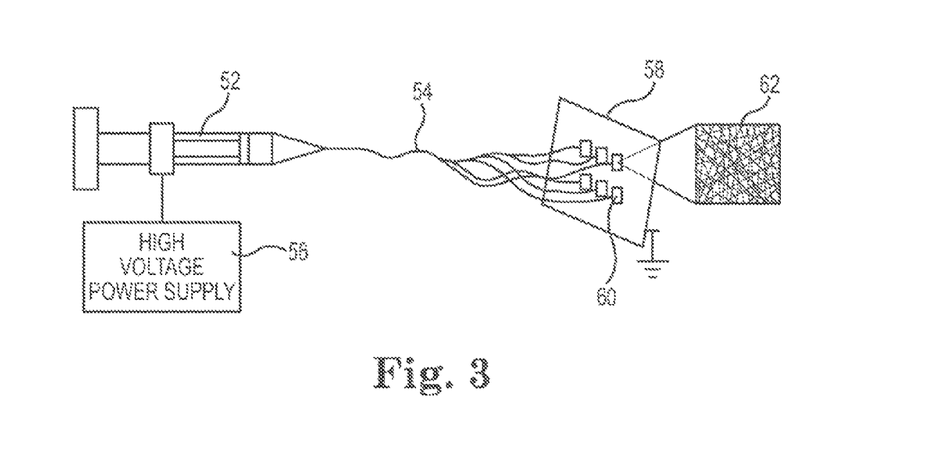
FIG. 3 is a schematic illustration of electrospinning.
Figure 4:
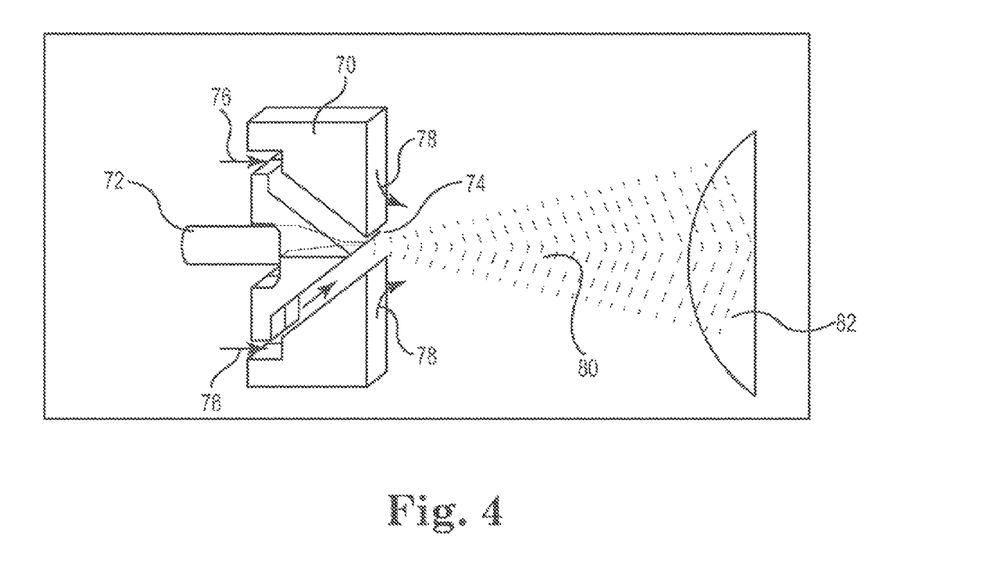
FIG. 4 is a schematic illustration of melt blowing.

The fibrous matrix 40 may be formed using several different techniques, such as electrospinning and melt blowing. In some embodiments, smaller fiber sizes may be achieved using electrospinning. FIGS. 3 and 4 schematically illustrate both techniques.

FIG. 3 provides a schematic illustration of electrospinning. An electric field may be used to draw a polymer solution or melt 54 from a capillary source 52. In some embodiments, the capillary source 52 may be a syringe. The polymer solution or melt 54 is drawn to a grounded collector 58. A high voltage power supply 56 may be used to power the process. The elements 60 to be coated may be placed on the collector 58 to be coated. Upon drying, a thin polymeric web 62 may be formed. In some embodiments, the fiber sizes may be controlled by adjusting the relative concentration of polymer in the polymer solution or melt 54.

The concentration of polymer in the electrospinning solution and solvent selection are important factors in achieving desired fibrous matrix properties, and in particular for controlling porosity and/or fiber size. Additionally, a small amount of a metal salt solution may be added to the electrospinning solution to improve deposition. In other embodiments, the electrospinning solution has a polymer concentration of between about 1 wt % and about 40 wt %, more particularly between about 1 wt % and about 30 wt %, even more particularly from about 3 wt % to about 15 wt %, and even more particularly from about 5 wt % to about 15 wt %. Suitable solvents include dimethylformamide, dimethylacetamide, N-methyl-2-pyrrolidone, dimethyl sulfoxide, acetone, cyclohexane tetrohydrofuran as well as mixtures and co-solvents thereof.

In other embodiments, the polymer may be a polyurethane polymer and the electrospinning solution may have a polymer concentration as little as 1%, 3% or 5%, or as great as 15%, 30% or 40% or may be within any range delimited by any pair of the foregoing values. In certain embodiments, the polymer may be a fluoropolymer and the electrospinning solution may have a polymer concentration as little as 5%, 10%, 15% or 20%, or as great as 30%, 35% or 40% or may be within any range delimited by any pair of the foregoing values.

FIG. 4 provides a schematic illustration of meltblowing. An apparatus 70 is configured to accommodate a polymer melt 72. The polymer melt 72 passes through an orifice 74 and is carried through the orifice 74 via streams of hot air 76 that pass through the apparatus 70. As the polymer melt 72 exits the orifice 74, they are met with streams of heated air 78 that helps elongate the polymer melt 72. As a result, the polymer melt 72 forms fibers 80 that impinge onto a collector 82. An element to be coated may simply be placed on or in front of the collector 82.

In some embodiments, the lead 10 may be assembled before the fibrous matrix 40 is formed directly on the lead 10.

In some embodiments, the fibrous matrix 40 may be formed on a component of the lead 10 before the lead 10 is assembled. In some embodiments, the fibrous matrix 40 may be separately formed and then subsequently disposed onto a portion of the lead 10.

In certain embodiments, the fibrous matrix may be formed from more than one polymer material in the form of a composite or material layers. In one example, a first layer comprising a first polymer material may be deposited onto a portion of the lead 10, followed by a second layer formed by a second polymer material. Additional layers may also be applied as desired. In another example, one of a plurality of layers comprises a non-conductive polymer material while another of the plurality of layers comprises a conductive material. In a further example, each layer comprises a non-conductive material.

Although the description herein discusses the fibrous matrix 40 on a lead 40, fibrous matrix 40 may be on any medical electrical device such as but not limited to implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), and cardiac resynchronization and defibrillation (CRDT) devices, among others.

Experimental Section

Impedance Testing

Comparative Samples A and B and Samples C-F

A group of coil pacing lead electrodes were tested for resistance over a series of 20 shocks at pulse intervals of 10 seconds. Comparative Samples A and B were pacemaker leads including commercially available electrodes produced with a tissue growth inhibition process. Samples C-F were formed from the same type of lead as Samples A and B but the electrodes were coated with a fibrous matrix of Tecothane 55D, commercially available polyether polyurethane, deposited on the electrode by electrospinning. To form the fibrous matrix, a coating solution containing 5 wt % Tecothane in dimethylacetamide was prepared. The coating solution was loaded into a single needle electrospinning apparatus approximately 10 centimeters (cm) from the electrode surface. The electrospinning apparatus was used to deposit the fibrous matrix onto the electrode under ambient conditions to form a coating thickness of approximately 0.051 mm (0.002 in.).

Figure 5:
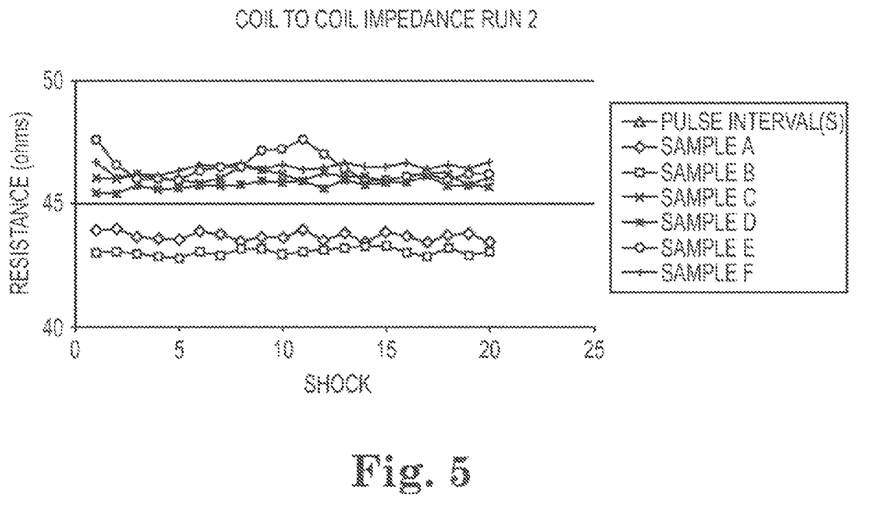
FIG. 5 is a graphical representation of experimental data.

FIG. 5 provides a graphical representation of the impedance testing. While Comparative Sample A and Sample B provide the lowest resistance and least variability, Samples C-F exhibited comparable resistance near 45 ohms over the course of the 20 pulses. This indicates that the fibrous matrix did not substantially increase the impedance of the electrode.

Comparative Sample G and Samples H-J

A group of coil pacing lead electrodes were tested for resistance over a series of 20 shocks at pulse intervals of 10 seconds. Comparative Sample G was a pacemaker lead including a commercially available electrode produced with a tissue growth inhibition process. Samples H, I and J were formed from the same type of lead as Comparative Sample G, but the electrodes were covered with a fibrous matrix of poly(vinylidene fluoride-co-hexafluoropropene)(PVDF HFP), a commercially available fluoropolymer including poly(vinylidene fluoride, deposited on the electrode by electrospinning. To form the fibrous matrix, a coating solution containing 25 wt % PVDF HFP in dimethylformamide was prepared. The coating solution was loaded into a single needle electrospinning apparatus approximately 10 centimeters from the electrode surface. The electrospinning apparatus was used to deposit the fibrous matrix onto the electrode under ambient conditions. Six leads were covered for each Sample with fibrous matrix thicknesses ranging from 0.018 mm to 0.051 mm (0.0007 in. to 0.002 inches). The samples were then treated with a poly(ethylene glycol)dimethacrylate solution to increase wettability.

Figure 6:
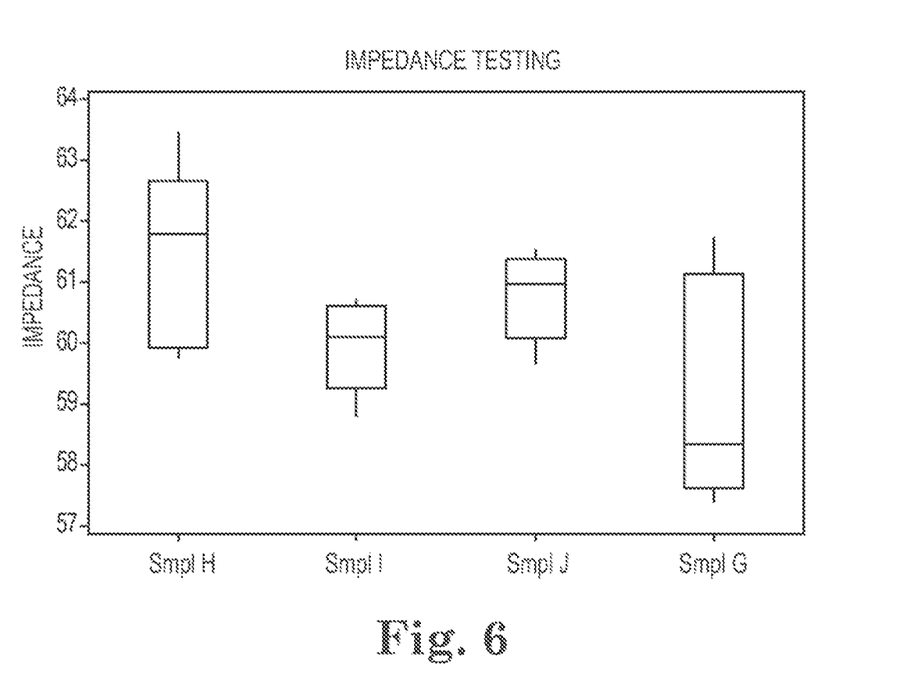
FIG. 6 is a graphical representation of experimental data.

FIG. 6 provides a graphical representation of the impedance testing. While Sample G provided the lowest resistance and least variability, Samples H-J exhibited comparable resistance over the course of the 20 pulses. This indicates that the fibrous matrix did not substantially increase the impedance of the electrode.

Tissue Extraction

A shocking coil was implanted subcutaneously into patient tissue. Thirty days after implantation, an incision was made at one end of the shocking coil. The end of the coil was excised out of the tissue and attached to an Instron force gauge. The maximum force to completely extract the coil from under the skin longitudinally was recorded. A greater the extraction force indicates a greater degree of tissue adhesion or tissue ingrowth. In some embodiments, a suitable product may have an extraction force less than or about equivalent to a currently commercially available product.

Samples K and L and Comparative Samples M and N

A group of shocking coils were tested for tissue extraction and tissue adhesion. Sample K included a polycarbonate urethane fibrous matrix, having an average fiber size of about 0.3 microns and Sample L included a polycarbonate urethane fibrous matrix having an average fiber size of about 0.750 microns. The fibrous matrixes of Samples K and L were formed by electrospinning and had a thicknesses ranging from 0.013 millimeters (mm) to 0.051 mm (0.0005 inches (in) to 0.002 in). Comparative Sample M and Comparative Sample N were commercially available coils produced by different tissue growth inhibition processes. The tissue extraction results in newtons (N) are provided in Table 1.

TABLE 1

|  | Sample K | Sample L | Comparative Sample M | Comparative Sample N |
|---|---|---|---|---|
| Average Max force (N) | 2.61 | 4.68 | 1.49 | 3.75 |
| Standard Deviation | 0.166 | 0.098 | 0.335 | 0.362 |

As shown in Table 1, a fibrous matrix having an average diameter of 0.3 microns (Sample K) required less force to extract than a fibrous matrix having an average diameter of about 0.750 microns (Sample L), illustrating that the extraction force required decreases with reduced fiber diameters. Further, Sample K required a slightly greater extraction force than commercially available coil Sample M and less force to extract than commercially available coil Sample N. Sample L required more force to extract than Sample M and Sample N. In some embodiments it may be desirable that the extraction force required for the fibrous matrix coated coil to be less than or equal to that of commercially available coils, such as Comparative Sample M and Comparative Sample N.

Samples O and P and Comparative Samples Q and R

The amount of force required to extract coils having a fibrous matrix including PVDF HFP were also investigated. Samples O and P included a PVDF HFP fibrous matrix having an average fiber diameter of about 0.730 microns. The fibrous matrixes of Samples O and P were formed by electrospinning and had a thickness ranging from 0.013 mm to 0.051 mm (0.0005 in to 0.002 in). Comparative Sample Q and Comparative Sample R were commercially available coils produced with different tissue growth inhibition processes. The tissue extraction results in newtons (N) are presented in Table 2.

TABLE 2

|  | Sample O | Sample P | Comparative Sample Q | Comparative Sample R |
|---|---|---|---|---|
| Average Max force (N) | 6.79 | 7.84 | 2.36 | 4.60 |
| Standard Deviation | 0.222 | 0.546 | 0.334 | 0.459 |

As shown in Table 2, fibrous matrixes containing PVDF HFP and having an average fiber size of about 0.730 microns required a larger force for extraction than Comparative Sample Q and Comparative Sample R. Sample O and Sample P suggest that PVDF HFP fibers having an average fiber diameter greater than about 0.730 microns may require undesirably high extraction forces.

Various modifications and additions can be made to the exemplary embodiments discussed without departing from the scope of the present invention. For example, while the embodiments described herein refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead comprising:
an insulative lead body extending from a distal region to a proximal region;
a conductor disposed within the insulative lead body and extending from the proximal region to the distal region;
an electrode disposed on the insulative lead body and in electrical contact with the conductor; and
a non-conductive fibrous matrix comprising polyether polyurethane disposed at least partially over the electrode, the fibrous matrix having an average fiber diameter between 40 nanometers and 800 nanometers, an average thickness between about 2.54 microns and about 254, and an average fiber-to-fiber spacing between about 10 microns to about 50 microns.

2. The medical electrical lead of claim 1, wherein the fibrous matrix comprises electrospun polyether polyurethane.

3. The medical electrical lead of claim 1, wherein the fibrous matrix has sufficient fiber-to-fiber spacing to deliver electrophysiological therapy through the matrix.

4. The medical electrical lead of claim 1, wherein the fibrous matrix has an average fiber-to-fiber spacing between about 10 microns to about 25 microns.

5. The medical electrical lead of claim 1, further including a material on a surface of the fibrous matrix, wherein the material increases wettability of the surface as compared to the surface without the material.

6. The medical electrical lead of claim 5, wherein the material is poly(ethylene glycol) dimethacrylate.

7. A method of forming a medical electrical lead having an insulative lead body and an electrode disposed on the insulative lead body, the method comprising steps of:
forming a fibrous matrix comprising polyether polyurethane polymer by electrospinning; and
disposing the fibrous matrix at least partially over the electrode;
wherein the fibrous matrix has an average fiber diameter between 40 nanometers and 800 nanometers an average thickness between about 2.54 microns and about 254, and an average fiber-to-fiber spacing between about 10 microns to about 50 microns.

8. The method of claim 7, wherein forming the fibrous matrix comprises forming the fibrous matrix directly onto the electrode.

9. The method of claim 7, wherein forming the fibrous matrix comprises forming the fibrous matrix on a substrate and then depositing the fibrous matrix at least partially over the electrode.

10. The method of claim 7, further including treating a surface of the fibrous matrix with a material that increases wettability of the surface as compared to the surface prior to the treating.

11. The method of claim 10, wherein the material is poly (ethylene glycol) dimethacrylate.

12. The method of claim 7, wherein the fibrous matrix has sufficient fiber-to-fiber spacing to deliver electrophysiological therapy through the matrix.

13. The method of claim 7, wherein the fibrous matrix has an average fiber-to-fiber spacing between about 10 microns to about 25 microns.

14. A medical electrical lead comprising:
an insulative lead body extending from a distal region to a proximal region;
a conductor disposed within the insulative lead body and extending from the proximal region to the distal region;
an electrode disposed on the insulative lead body and in electrical contact with the conductor; and
a fibrous matrix comprising electrospun polyether polyurethane disposed at least partially over the electrode, the fibrous matrix having an average fiber diameter between 40 nanometers and 800 nanometers, and an average fiber-to-fiber spacing between about 10 microns to about 50 microns.

15. The medical electrical lead of claim 14, further including a material on a surface of the fibrous matrix, wherein the material increases wettability of the surface as compared to the surface without the material.

16. The medical electrical lead of claim 14, wherein the fibrous matrix has an average fiber-to-fiber spacing between about 10 microns to about 25 microns.

17. The medical electrical lead of claim 14, wherein the fibrous matrix further includes dopant material to facilitate polymer conductivity.

18. The medical electrical lead of claim 17, wherein the dopant material is less than 5 weight percent of the fibrous matrix.

* * * * *